(12) United States Patent
Wang et al.

(10) Patent No.: US 9,878,065 B2
(45) Date of Patent: Jan. 30, 2018

(54) STIFF NANOCOMPOSITE FILM FOR USE IN AN ABSORBENT ARTICLE

(71) Applicant: Kimberly-Clark Worldwide, Inc., Neenah, WI (US)

(72) Inventors: James Hongxue Wang, Appleton, WI (US); Feng Chen, Neenah, WI (US); Gregory J. Wideman, Neenah, WI (US); Michael J. Faulks, Neenah, WI (US); Mark M. Mleziva, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/914,263

(22) PCT Filed: Jan. 30, 2015

(86) PCT No.: PCT/US2015/013821
§ 371 (c)(1),
(2) Date: Feb. 25, 2016

(87) PCT Pub. No.: WO2015/116953
PCT Pub. Date: Aug. 6, 2015

(65) Prior Publication Data
US 2016/0325005 A1    Nov. 10, 2016

Related U.S. Application Data

(60) Provisional application No. 61/934,434, filed on Jan. 31, 2014.

(51) Int. Cl.
*A61F 13/15* (2006.01)
*A61L 15/22* (2006.01)
(Continued)

(52) U.S. Cl.
CPC ...... *A61L 15/225* (2013.01); *A61F 13/15731* (2013.01); *A61F 13/47* (2013.01);
(Continued)

(58) Field of Classification Search
CPC ........ A61L 15/225; A61L 15/18; A61L 15/20; A61L 15/24; A61L 15/42; A61L 15/46;
(Continued)

(56) References Cited

U.S. PATENT DOCUMENTS 3,354,506 A    11/1967 Raley
3,650,649 A    3/1972 Schippers
(Continued)

FOREIGN PATENT DOCUMENTS

RU    2007134346 A    3/2009
RU    2009123011 A    12/2010
(Continued)

OTHER PUBLICATIONS

Chen et al. PCT/US2015/013851 filed Jan. 30, 2015 Absorbent Article Package with Reduced Noise.
(Continued)

*Primary Examiner* — Jacqueline Stephens
(74) *Attorney, Agent, or Firm* — Dority & Manning, P.A.

(57) ABSTRACT

A thin nanocomposite film for use in an absorbent article (e.g., sanitary napkin) is provided. The film contains a first ethylene polymer having a density of about 0.94 g/cm3 or less, second ethylene polymer having a density of greater than 0.94 g/cm3, and nanoclay having an organic surface treatment. The present inventors have discovered that through selective control over the particular type and concentration of the components used to form the film, as well as the manner in which it is formed, the properties of the film can be significantly improved.

32 Claims, 5 Drawing Sheets

(51) Int. Cl.
| | |
|---|---|
| A61F 13/51 | (2006.01) |
| A61F 13/47 | (2006.01) |
| A61F 13/472 | (2006.01) |
| A61L 15/18 | (2006.01) |
| A61L 15/24 | (2006.01) |
| A61L 15/42 | (2006.01) |
| A61L 15/46 | (2006.01) |
| A61F 13/514 | (2006.01) |
| A61F 13/56 | (2006.01) |
| A61L 15/20 | (2006.01) |
| A61L 15/60 | (2006.01) |
| C08J 5/18 | (2006.01) |
| C08L 23/06 | (2006.01) |
| B29C 47/00 | (2006.01) |
| B29K 23/00 | (2006.01) |
| B29K 105/16 | (2006.01) |
| B29K 509/00 | (2006.01) |
| B29L 31/48 | (2006.01) |

(52) U.S. Cl.
CPC ........ *A61F 13/472* (2013.01); *A61F 13/4702* (2013.01); *A61F 13/51* (2013.01); *A61F 13/51401* (2013.01); *A61F 13/5616* (2013.01); *A61L 15/18* (2013.01); *A61L 15/20* (2013.01); *A61L 15/24* (2013.01); *A61L 15/42* (2013.01); *A61L 15/46* (2013.01); *A61L 15/60* (2013.01); *C08J 5/18* (2013.01); *C08L 23/06* (2013.01); *A61F 2013/15292* (2013.01); *A61F 2013/15422* (2013.01); *A61F 2013/15715* (2013.01); *A61F 2013/51023* (2013.01); *A61F 2013/51409* (2013.01); *B29C 47/0004* (2013.01); *B29C 47/0026* (2013.01); *B29K 2023/065* (2013.01); *B29K 2023/0625* (2013.01); *B29K 2105/162* (2013.01); *B29K 2509/00* (2013.01); *B29L 2031/4878* (2013.01); *C08J 2323/06* (2013.01); *C08L 2203/16* (2013.01); *C08L 2207/062* (2013.01); *C08L 2207/066* (2013.01); *C08L 2310/00* (2013.01)

(58) Field of Classification Search
CPC ...... A61L 15/60; A61F 13/47; A61F 13/4702; A61F 13/51; A61F 13/51401; A61F 13/5616; C08J 5/18
USPC ........................ 604/366, 367, 385.04, 385.23
See application file for complete search history.

(56) References Cited

U.S. PATENT DOCUMENTS

| | | | |
|---|---|---|---|
| 3,801,429 A | 4/1974 | Schrenk et al. | |
| 4,041,203 A | 8/1977 | Brock et al. | |
| 4,374,888 A | 2/1983 | Bornslaeger | |
| 4,704,116 A | 11/1987 | Enloe | |
| 4,728,325 A * | 3/1988 | Spiller .................... | A61L 15/24 524/240 |
| 4,766,029 A | 8/1988 | Brock et al. | |
| 4,789,699 A | 12/1988 | Kieffer et al. | |
| 4,798,603 A | 1/1989 | Meyer et al. | |
| 4,886,512 A | 12/1989 | Damico et al. | |
| 4,897,449 A * | 1/1990 | Gaillard ................ | C08F 285/00 524/504 |
| 5,102,948 A | 4/1992 | Deguchi et al. | |
| 5,169,706 A | 12/1992 | Collier, IV et al. | |
| 5,192,606 A | 3/1993 | Proxmire et al. | |
| 5,213,881 A | 5/1993 | Timmons et al. | |
| 5,248,309 A | 9/1993 | Serbiak et al. | |
| 5,254,111 A | 10/1993 | Cancio et al. | |
| 5,272,236 A | 12/1993 | Lai et al. | |
| 5,322,728 A | 6/1994 | Davey et al. | |
| 5,464,688 A | 11/1995 | Timmons et al. | |
| 5,472,775 A | 12/1995 | Obijeski et al. | |
| 5,486,166 A | 1/1996 | Bishop et al. | |
| 5,490,846 A | 2/1996 | Ellis et al. | |
| 5,558,659 A | 9/1996 | Sherrod et al. | |
| 5,571,619 A | 11/1996 | McAlpin et al. | |
| 5,649,916 A | 7/1997 | DiPalma et al. | |
| 5,695,868 A | 12/1997 | McCormack | |
| 5,702,377 A | 12/1997 | Collier, IV et al. | |
| 5,853,886 A | 12/1998 | Pinnavaia et al. | |
| 5,877,248 A | 3/1999 | Beall et al. | |
| 5,880,197 A | 3/1999 | Beall et al. | |
| 5,931,823 A | 8/1999 | Stokes et al. | |
| 6,060,638 A | 5/2000 | Paul et al. | |
| 6,090,325 A | 7/2000 | Wheat et al. | |
| 6,110,158 A | 8/2000 | Kielpikowski | |
| 6,150,002 A | 11/2000 | Varona | |
| 6,380,445 B1 | 4/2002 | Rietz et al. | |
| 6,455,161 B1 | 9/2002 | Regnier et al. | |
| 6,511,465 B1 | 1/2003 | Freiburger et al. | |
| 6,663,611 B2 | 12/2003 | Blaney et al. | |
| 6,716,203 B2 | 4/2004 | Sorebo et al. | |
| 6,812,272 B2 | 11/2004 | Fischer | |
| 6,824,734 B2 | 11/2004 | Boggs et al. | |
| 6,846,532 B1 | 1/2005 | Bensur | |
| 6,888,044 B2 | 5/2005 | Fell et al. | |
| 7,060,867 B2 | 6/2006 | Jameson | |
| 7,553,898 B2 | 6/2009 | Rafailovich et al. | |
| 7,837,899 B2 | 11/2010 | Moad et al. | |
| 7,872,169 B2 | 1/2011 | Ruiz et al. | |
| 8,198,200 B2 | 6/2012 | Autran et al. | |
| 8,323,258 B2 | 12/2012 | Dalal et al. | |
| 8,518,313 B2 | 8/2013 | Szekely | |
| 8,518,318 B2 | 8/2013 | Jacobs | |
| 8,722,804 B2 | 5/2014 | Lue et al. | |
| 2003/0116462 A1 | 6/2003 | Sorebo et al. | |
| 2004/0060112 A1 | 4/2004 | Fell et al. | |
| 2004/0078015 A1 | 4/2004 | Copat et al. | |
| 2005/0054255 A1 | 3/2005 | Morman et al. | |
| 2005/0059941 A1 | 3/2005 | Baldwin et al. | |
| 2005/0112338 A1 * | 5/2005 | Faulks .............. | A61F 13/51405 428/204 |
| 2005/0222327 A1 * | 10/2005 | Botros ................ | C08F 255/02 525/64 |
| 2005/0245162 A1 | 11/2005 | McCormack et al. | |
| 2006/0094810 A1 | 5/2006 | Kim et al. | |
| 2007/0264897 A1 * | 11/2007 | Collias ................ | C08J 5/18 442/417 |
| 2010/0092793 A1 | 4/2010 | Aithani et al. | |
| 2010/0121295 A1 | 5/2010 | Collias et al. | |
| 2010/0178477 A1 | 7/2010 | Jacobs | |
| 2011/0028633 A1 | 2/2011 | Moad et al. | |
| 2011/0263776 A1 | 10/2011 | Debras et al. | |
| 2012/0039975 A1 | 2/2012 | Lagaron Cabello et al. | |
| 2012/0238682 A1 | 9/2012 | Yang et al. | |
| 2012/0315454 A1 | 10/2012 | De La Bruniere | |
| 2012/0321856 A1 | 12/2012 | Afshari | |

FOREIGN PATENT DOCUMENTS

| | | |
|---|---|---|
| WO | WO 2007/121048 A1 | 10/2007 |
| WO | WO2015/116958 | 8/2015 |
| WO | WO2015/116965 | 8/2015 |

OTHER PUBLICATIONS

Chen et al. PCT/US2015/013861 filed Jan. 30, 2015 Film with Reduced Noise For Use in an Absorbent Article.
International Search Report and Written Opinion for PCT/US2015/013821, dated Apr. 27, 2015, 11 pages.
Related U.S. Patent Applications Form.

* cited by examiner

STIFF NANOCOMPOSITE FILM FOR USE IN AN ABSORBENT ARTICLE

CROSS REFERENCE TO RELATED APPLICATIONS

This application is the national stage entry of International Patent Application No. PCT/US2015/13821 having a filing date of Jan. 30, 2015, which claims priority to U.S. Provisional Patent Application Ser. No. 61/934,434 having a filing date of Jan. 31, 2014, which are incorporated herein in their entirety by reference thereto.

BACKGROUND OF THE INVENTION

Feminine care absorbent articles, such as sanitary napkins, are generally constructed from an absorbent core that is positioned between a liquid-permeable topsheet, which defines a "body-facing" surface disposed toward the body, and a liquid-impermeable backsheet, which defines a "garment-facing" surface disposed away from the body. Such articles often contain flaps or wings that extend laterally from an edge of the article and can attach around the side edges of a wearer's undergarments. The wings may be formed from a linear low density polyethylene ("LLDPE") film, which can be optionally laminated to a polypropylene nonwoven web. One of the problems with these films, however, is that they often lack enough stiffness and strength to enable the production process of the absorbent articles and help support the article during use. While attempts have been made to add various additives to the film to improve these properties, this usually results in a corresponding decrease in other properties (e.g., ductility), which is highly undesirable. As such, a need currently exists for a film for use in an absorbent article that can exhibit good stiffness and strength without a substantial reduction in other properties.

SUMMARY OF THE INVENTION

In accordance with one embodiment of the present invention, an absorbent article is disclosed that comprises a liquid permeable layer, a generally liquid-impermeable layer, and an absorbent core positioned between the liquid permeable layer and the generally liquid-impermeable layer. The absorbent article contains a film having a thickness of about 50 micrometers or less. The film contains a layer that is formed from a polymer composition, wherein the polymer composition contains a first ethylene polymer having a density of about 0.94 g/cm$^3$ or less, a second ethylene polymer having a density of greater than 0.94 g/cm$^3$, and a nanoclay having an organic surface treatment. The weight ratio of the first ethylene polymer to the second ethylene polymer is from about 0.1 to about 10.

In accordance with another embodiment of the present invention, a film having a thickness of about 50 micrometers or less is disclosed. The film contains a layer that is formed from a polymer composition. The polymer composition contains from about 5 wt. % to about 90 wt. % of a first ethylene polymer having a density of about 0.94 g/cm$^3$ or less, from about 5 wt. % to about 90 wt. % of a second ethylene polymer having a density of greater than 0.94 g/cm$^3$, and from about 0.5 wt. % to about 20 wt. % of a nanoclay having an organic surface treatment. The weight ratio of the first ethylene polymer to the second ethylene polymer is from about 0.1 to about 10, and the film exhibits a Young's modulus in the machine direction of from about 150 to about 1000 Megapascals.

Other features and aspects of the present invention are described in more detail below.

BRIEF DESCRIPTION OF THE DRAWING

A full and enabling disclosure of the present invention, including the best mode thereof, directed to one of ordinary skill in the art, is set forth more particularly in the remainder of the specification, which makes reference to the appended figures in which.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a thin nanocomposite film for use in an absorbent article (e.g., sanitary napkin). The film contains a first ethylene polymer having a density of about 0.94 g/cm$^3$ or less (e.g., LLDPE and/or LDPE), second ethylene polymer having a density of greater than 0.94 g/cm$^3$ (e.g., HDPE), and at least one nanoclay having an organic surface treatment. The weight ratio of the first ethylene polymer to the second ethylene polymer may be from about 0.1 to about 10, in some embodiments from about 0.15 to about 8, and in some embodiments, from about 0.2 to about 5. For example, the first ethylene polymer may constitute from about 5 wt. % to about 90 wt. %, in some embodiments from about 10 wt. % to about 80 wt. %, and in some embodiments, from about 20 wt. % to 70 wt. % of the polymer composition and the second ethylene polymer may constitute from about 5 wt. % to about 90 wt. %, in some embodiments from about 10 wt. % to about 80 wt. %, and in some embodiments, from about 20 wt. % to 70 wt. % of the polymer composition. The nanoclay may likewise constitute from about 0.5 wt. % to about 20 wt. %, in some embodiments from about 1 wt. % to about 15 wt. %, and in some embodiments, from about 2 wt. % to about 10 wt. % of the polymer composition.

The present inventors have discovered that through selective control over the particular type and concentration of the components used to form the film, as well as the manner in which it is formed, the stiffness of the film can be significantly improved without having an adverse impact on its strength and ductility. One parameter that is indicative of good stiffness is the Young's modulus of elasticity of the film, which is equal to the ratio of the tensile stress to the tensile strain and is determined from the slope of a stress-strain curve, may also be good. For example, the film typically exhibits a Young's modulus in the machine direction of from about 150 to about 1000 MPa, in some embodiments from about 200 to about 800 MPa, and in some embodiments, from about 300 to about 700 MPa, and in the cross-machine direction of from about 200 to about 1200 MPa, in some embodiments from about 250 to about 1000 MPa, and in some embodiments, from about 350 to about 800 MPa. Despite having such improved stiffness, the film of the present invention is nevertheless able to retain good mechanical strength and ductility. For example, the film of the present invention may exhibit an ultimate tensile strength in the machine direction and/or cross-machine direction of from about 15 to about 150 Megapascals (MPa), in some embodiments from about 20 to about 100 MPa, and in some embodiments, from about 25 to about 80 MPa. The film may also exhibit a peak elongation in the machine direction of about 200% or more, in some embodiments about 250% or more, and in some embodiments, from about 300% to about 400%, and in the cross-machine direction of about 700% or more, in some embodiments about 750% or more, and in some embodiments, from about 800% to about 1500%.

Surprisingly, such good properties can be achieved even though the film has a very low thickness. In this regard, the normalized mechanical properties, which are determined by dividing a particular mechanical value (e.g., Young's modulus, tensile strength, or peak elongation) by the average film thickness (µm), may also be improved. For example, the film may exhibit a normalized peak elongation in the machine direction of about 10%/µm or more, in some embodiments about 15%/µm or more, and in some embodiments, from about 20%/µm to about 100%/µm. The film may likewise exhibit a normalized peak elongation in the cross-machine direction of about 40%/µm or more, in some embodiments about 50%/µm or more, and in some embodiments, from about 60%/µm to about 200%/µm. The film may exhibit a normalized ultimate tensile strength in the machine direction and/or cross-machine direction of from about 0.5 to about 20 MPa/µm, in some embodiments from about 1 to about 12 MPa/µm, and in some embodiments, from about 2 to about 8 MPa/µm. The normalized Young's modulus in the machine direction and/or cross-machine direction may also be from about 5 to about 60 MPa/µm, in some embodiments from about 15 to about 50 MPa/µm, and in some embodiments, from about 25 to about 45 MPa/µm. The actual thickness of the film is typically about 50 micrometers or less, in some embodiments from about 1 to about 40 micrometers, in some embodiments from about 5 to about 35 micrometers, and in some embodiments from about 10 to about 30 micrometers.

The present inventors have also discovered that the film may generate a relatively low degree of noise when physically deformed. When subjected to physical deformation for two (2) minutes, for instance, the noise level of the film may be about 45 decibels (dB) or less, in some embodiments about 42 dB or less, and in some embodiments, from about 20 dB to about 40 dB, such as determined at a frequency of 2,000 Hz or 4,000 Hz. The "normalized noise level" of the film, which is determined by dividing the noise level of the film that is generated while the film is subjected to physical deformation for two (2) minutes by the noise level generated by an ambient environment, may likewise be about 2.5 or less, in some embodiments about 2.4 or less, and in some embodiments, from about 1.5 to about 2.3, such as determined at a frequency of 2,000 Hz or 4,000 Hz. The entire absorbent article may also exhibit a relatively low degree of noise. For instance, when subjected to physical deformation for two (2) minutes, the noise level generated by the absorbent article may be about 30 decibels (dB) or less, in some embodiments about 29 dB or less, and in some embodiments, from about 20 dB to about 28 dB, as determined at a frequency of 2000 Hz. The "normalized noise level" of the absorbent article may likewise be about 1.55 or less, in some embodiments about 1.50 or less, and in some embodiments, from about 0.5 to about 1.45, such as determined at a frequency of 2,000 Hz or 4,000 Hz.

In addition to a reduced noise level, the film of the present invention may also have excellent barrier properties to oxygen transmission. Without intending to be limited by theory, it is believed that the nanoclay platelet structure can create a tortuous pathway in the film, which may slow down the transmission rate and reduce the amount of permeant oxygen. For example, the oxygen transmission rate may be about 350 $cm^3/100$ $in^2$*24-hours or less, in some embodiments about 330 $cm^3/100$ $in^2$*24-hours or less, and in some embodiments, from about 100 to about 300 $cm^3/100$ $in^2$*24-hours, such as determined in accordance with ASTM D3985-05 at a temperature of 23° C. and a relative humidity of 0%.

Various embodiments of the present invention will now be described in more detail.

I. Polymer Composition

A. First Ethylene Polymer

As indicated above, the first ethylene polymer has a relatively low density in the range of about 0.94 $g/cm^3$ or less, in some embodiments from about 0.85 to about 0.94 $g/cm^3$, and in some embodiments, from about 0.90 to about 0.935 $g/cm^3$. One or more polymers may be employed in the composition that has these density characteristics. Linear low density polyethylene ("LLDPE") and/or low density polyethylene ("LDPE") are particularly suitable. The first ethylene polymer typically has a relatively low melting temperature and modulus of elasticity, which can provide the resulting film with a relatively soft and ductile feel. For example, the first ethylene polymer may have a melting temperature of from about 50° C. to about 145° C., in some embodiments from about 75° C. to about 140° C., and in some embodiments, from about 100° C. to about 135° C., and a modulus of elasticity of from about 50 to about 700 MPa, in some embodiments from about 75 to about 600 MPa, and in some embodiments, from about 100 to about 500 MPa, as determined in accordance with ASTM D638-10. The first ethylene polymer may also have a melt flow index of from about 0.1 to about 100 grams per 10 minutes, in some embodiments from about 0.5 to about 50 grams per 10 minutes, and in some embodiments, from about 1 to about 40 grams per 10 minutes, determined at a load of 2160 grams and at 190° C., as determined in accordance with ASTM D1238-13 (or ISO 1133).

B. Second Ethylene Polymer

Contrary to the first polymer, the second ethylene polymer has a relatively high density in the range of greater than about 0.94 $g/cm^3$, in some embodiments from about 0.945 to about 0.98 $g/cm^3$, and in some embodiments, from about 0.95 to about 0.97 $g/cm^3$. Once again, one or more polymers may be employed in the composition that has these characteristics. High density polyethylene ("HDPE") is particularly suitable. The second ethylene polymer typically has a relatively low melting temperature and modulus of elasticity, which can provide the resulting film with a relatively soft and ductile feel. For example, the first ethylene polymer may have a melting temperature of from about 70° C. to about 160° C., in some embodiments from about 85° C. to about 150° C., and in some embodiments, from about 110° C. to about 145° C., and a modulus of elasticity of from about 700 to about 5,000 MPa, in some embodiments from about 750 to about 3,000 MPa, and in some embodiments, from about 1,000 to about 2,000 MPa, as determined in accordance with ASTM D638-10. The second ethylene polymer may also have a melt flow index of from about 0.1 to about 100 grams per 10 minutes, in some embodiments from about 0.5 to about 50 grams per 10 minutes, and in some embodiments, from about 1 to about 40 grams per 10 minutes, determined at a load of 2160 grams and at 190° C., as determined in accordance with ASTM D1238-13 (or ISO 1133).

The first and/or second ethylene polymer may be formed from any type of ethylene polymer as is known in the art. The ethylene polymers may, for example, be a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %. The density of the polyethylene may vary depending on the type of polymer employed, but generally ranges from about 0.85 to about 0.96 grams per cubic centimeter (g/cm$^3$).

Various known techniques may generally be employed to form ethylene polymers. For instance, ethylene polymers may be formed using a free radical or a coordination catalyst (e.g., Ziegler-Natta). Typically, the ethylene polymer is formed from multi-site Ziegler-Natta catalysts, the resulting ethylene polymer has a broad molecular weight distribution with a polydispersity index (weight average molecular weight divided by number average molecular weight) of up to 20 or higher. The ethylene polymer made by a single-site coordination catalyst, such as a metallocene catalyst, has a narrow molecular weight distribution. Such a catalyst system produces ethylene polymers in which a comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al. Examples of metallocene catalysts include bis(n-butylcyclopentadienyl)titanium dichloride, bis(n~butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-fluorenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

B. Nanoclay

The term "nanoclay" generally refers to nanoparticles of a clay material (a naturally occurring mineral, an organically modified mineral, or a synthetic nanomaterial). The clay material typically has a flake-like morphology in that it possesses a relatively flat or platelet shape. The clay platelets may, for example, have an average thickness of from about 0.2 to about 100 nanometers, in some embodiments from about 0.5 to about 50 nanometers, and in some embodiments, from about 1 to about 20 nanometers. The "aspect ratio" of the clay material (i.e., the average length of the platelets divided by the average thickness) is also relatively large, such as from about 20 to about 1000, in some embodiments from about 50 to about 80, in some embodiments, from about 100 to about 400. The average length (e.g., diameter) may, for instance, range from about 20 nanometers to about 10 micrometers, in some embodiments from about 100 nanometers to about 5 micrometers, and in some embodiments, from about 200 nanometers to about 4 micrometers.

The clay material may be formed from a phyllosilicate, such as a smectite clay mineral (e.g., bentonite, kaolinite, or montmorillonite, as well as salts thereof, such as sodium montmorillonite, magnesium montmorillonite, calcium montmorillonite, etc.); nontronite; beidellite; volkonskoite; hectorite; saponite; sauconite; sobockite; stevensite; svinfordite; vermiculite; etc. Other useful nanoclays include micaceous minerals (e.g., illite) and mixed illite/smectite minerals, such as rectorite, tarosovite, ledikite and admixtures of illites with the clay minerals named above. Particularly suitable are montmorillonite (2:1 layered smectite clay structure), bentonite (aluminium phyllosilicate formed primarily of montmorillonite), kaolinite (1:1 aluminosilicate having a platy structure and empirical formula of $Al_2Si_2O_5(OH)_4$), halloysite (1:1 aluminosilicate having a tubular structure and empirical formula of $Al_2Si_2O_5(OH)_4$), etc.

As noted above, the nanoclay also contains an organic surface treatment that enhances the hydrophobicity of the clay material and thus improves its compatibility with the ethylene polymer. In one embodiment, the organic surface treatment may be formed from a quaternary onium (e.g., salt or ion), which may become intercalated via ion-exchange into the interlayer spaces between adjacent layered clay platelets. The quaternary onium ion may have the following structure:

wherein

X is N, P, S, or O; and $R_1$, $R_2$, $R_3$ and $R_4$ are independently hydrogen or organic moieties, such as linear or branched alkyl, aryl or aralkyl moieties having 1 to about 24 carbon atoms.

Particularly suitable quaternary ammonium ions are those having the structure below:

wherein $R_1$ is a long chain alkyl moiety ranging from $C_6$ to $C_{24}$, straight or branched chain, including mixtures of long chain moieties, such as $C_6$, $C_8$, $C_{10}$, $C_{12}$, $C_{14}$, $C_{16}$, $C_{18}$, $C_{20}$, $C_{22}$ and $C_{24}$, alone or in any combination; and $R_2$, $R_3$ and $R_4$ are moieties, which may be the same or different, selected from the group consisting of H, alkyl, hydroxyalkyl, benzyl, substituted benzyl, e.g., straight or branched chain alkyl-substituted and halogen-substituted; ethoxylated or propoxylated alkyl; ethoxylated or propoxylated benzyl (e.g., 1-10 moles of ethoxylation or 1-10 moles of propoxylation).

Additional useful multi-charged spacing/coupling agents include for example, tetra-, tri-, and di-onium species such as tetra-ammonium, tri-ammonium, and di-ammonium (primary, secondary, tertiary, and quaternary), -phosphonium, -oxonium, or -sulfonium derivatives of aliphatic, aromatic or arylaliphatic amines, phosphines, esters, alcohols and sulfides. Illustrative of such materials are di-onium compounds of the formula:

where $X^+$ and $Y^+$, are the same or different, and are ammonium, sulfonium, phosphonium, or oxonium radicals such as $-NH(CH_3)_2^+$, $-NH_2(CH_3)^+$, $-N(CH_3)_3^+$, $-N(CH_3)_2(CH_2CH_3)^+$, $-N(CH_3)(CH_2CH_3)_2^+$, $-S(CH_3)_2^+$, $-S(CH_3)_2^+$, $-P(CH_3)_3^+$, $-NH_3^+$, etc.;

R is an organic spacing, backbone radical, straight or branched, such as those having from 2 to 24 carbon atoms, and in some embodiments from 3 to 10 carbon atoms, in a backbone organic spacing molecule covalently bonded at its ends to charged $N^+$, $P^+$, $S^+$ and/or $O^+$ cations;

$R^1$ can be hydrogen, or a linear or branched alkyl radical of 1 to 22 carbon atoms, linear or branched, and in some embodiments, 6 to 22 carbon atoms.

Illustrative of useful R groups are alkyls (e.g., methyl, ethyl, butyl, octyl, etc.); aryl (e.g., benzyl, phenylalkyl, etc.); alkylenes (e.g., methylene, ethylene, octylene, nonylene, tert-butylene, neopentylene, isopropylene, sec-butylene, dodecylene, etc.); alkenylenes (e.g., 1-propenylene, 1-butenylene, 1-pentenylene, 1-hexenylene, 1-heptenylene, 1-octenylene, etc.); cycloalkenylenes (e.g., cyclohexenylene, cyclopentenylene, etc.); hydroxyalkyl (e.g. hydroxymethyl, hydroxyethyl, hydroxyl-n-propyl, hydroxyisopropyl, hydroxyl-n-butyl, hydroxyl-iso-butyl, hydroxyl-tert-butyl, etc.), alkanoylalkylenes (e.g., butanoyl octadecylene, pentanoyl nonadecylene, octanoyl pentadecylene, ethanoyl undecylene, propanoyl hexadecylene, etc.); alkylaminoalkylenes (e.g., methylamino octadecylene, ethylamino pentadecylene, butylamino nonadecylene, etc.); dialkylaminoalkylene (e.g., dimethylamino octadecylene, methylethylamino nonadecylene, etc.); arylaminoalkylenes (e.g., phenylamino octadecylene, p-methylphenylamino nonadecylene, etc.); diarylaminoalkylenes (e.g., diphenylamino pentadecylene, p-nitrophenyl-p'-methylphenylamino octadecylene, etc.); alkylarylaminoalkylenes (e.g., 2-phenyl-4-methylamino pentadecylene, etc.); alkylsulfinylenes, alkylsulfonylenes, alkylthio, arylthio, arylsulfinylenes, and arylsulfonylenes (e.g., butylthio octadecylene, neopentylthio pentadecylene, methylsulfinylnonadecylene, benzylsulfinyl pentadecylene, phenylsulfinyl octadecylene, propylthiooctadecylene, octylthio pentadecylene, nonylsulfonyl nonadecylene, octylsulfonyl hexadecylene, methylthio nonadecylene, isopropylthio octadecylene, phenylsulfonyl pentadecylene, methylsulfonyl nonadecylene, nonylthio pentadecylene, phenylthio octadecylene, ethylthio nonadecylene, benzylthio undecylene, phenethylthio pentadecylene, sec-butylthio octadecylene, naphthylthio undecylene, etc.); alkoxycarbonylalkylenes (e.g., methoxycarbonylene, ethoxycarbonylene, butoxycarbonylene, etc.); cycloalkylenes (e.g., cyclohexylene, cyclopentylene, cyclooctylene, cycloheptylene, etc.); alkoxyalkylenes (e.g., methoxymethylene, ethoxymethylene, butoxymethylene, propoxyethylene, pentoxybutylene, etc.); aryloxyalkylenes and aryloxyarylenes (e.g., phenoxyphenylene, phenoxymethylene, etc.); aryloryalkylenes (e.g., phenoxydecylene, phenoxyoctylene, etc.); arylalkylenes (e.g., benzylene, phenthylene, 8-phenyloctylene, 10-phenyldecylene, etc.); alkylarylenes (e.g., 3-decylphenylene, 4-octylphenylene, 4-nonylphenylene, etc.); and polypropylene glycol and polyethylene glycol substituents (e.g., ethylene, propylene, butylene, phenylene, benzylene, tolylene, p-styrylene, p-phenylmethylene, octylene, dodecylene, octadecylene, methoxyethylene, etc.), as well as combinations thereof. Such tetra-, tri-, and di-ammonium, -sulfonium, -phosphonium, -oxonium; ammonium/sulfonium; ammonium/phosphonium; ammoniumloxonium; phosphonium/oxonium; sulfonium/oxonium; and sulfonium/phosphonium radicals are well known in the art and can be derived from the corresponding amines, phosphines, alcohols or ethers, and sulfides.

Particularly suitable multi-charged spacing/coupling agent compounds are multi-onium ion compounds that include at least two primary, secondary, tertiary or quaternary ammonium, phosphonium, sulfonium, and/or oxonium ions having the following general formula:

wherein

R is an alkylene, aralkylene or substituted alkylene charged atom spacing moiety; and $Z_1$, $Z_2$, $R_1$, $R_2$, $R_3$, and $R_4$ may be the same or different and selected from the group consisting of hydrogen, alkyl, aralkyl, benzyl, substituted benzyl (e.g., e.g., straight or branched chain alkyl-substituted and halogen-substituted); ethoxylated or propoxylated alkyl; ethoxylated or propoxylated benzyl (e.g., 1-10 moles of ethoxylation or 1-10 moles of propoxylation).

Particularly suitable organic cations may include, for instance, quaternary ammonium compounds, such as dimethyl bis[hydrogenated tallow] ammonium chloride (2M2HT), methyl benzyl bis[hydrogenated tallow] ammonium chloride (MB2HT), methyl tris[hydrogenated tallow alkyl] chloride (M3HT), etc. An example of a suitable nanoclay is Nanomer™ 1.44P, which is a quaternary ammonium modified montmorillonite nanoclay and commercially available from Nanocor, Inc. Other suitable nanoclay additives include those available from Southern Clay Products, such as Cloisite™ 15A, Cloisite™ 30B, Cloisite™ 93A, and Cloisite™ Na+.

The onium ion may be introduced into (sorbed within) the interlayer spaces of the clay material in a number of ways. In one method, for example, the clay material is slurried in water, and the onium ion compound is dissolved therein. If necessary, the onium ion compound can be dissolved first in an organic solvent (e.g., propanol). If desired, the nanoclay may also be intercalated with an oligomer and/or polymer intercalant as is known in the art. For example, an olefin polymer or oligomer (e.g., ethylene polymer) intercalant may be employed. To intercalate an onium ion and an olefin intercalant between adjacent phyllosilicate platelets and optionally separate (exfoliate) the layered material into individual platelets, for example, the clay material may be first contacted with the onium ion and simultaneously or thereafter contacted with the melted oligomer/polymer intercalant to the onium ion-intercalated layered material. This may be accomplished, for instance, by directly compounding the materials in an extruder. Alternatively, the oligomer/polymer can be intercalated by an emulsion process by vigorously mixing with an emulsifier. If desired, a coupling agent (e.g., silane coupling agent) may also be employed to help bond the intercalant with the clay material. For example, the clay material may be initially treated with a coupling agent followed by ion-exchange of onium ions between the clay material, prior to or simultaneously with intercalation of the oligomer(s) or polymer(s). It should be understood that the oligomer or polymer intercalant(s) can also be intercalated between and complexed to the internal platelet faces by other well-known mechanisms, such as by dipole/dipole bonding (direct intercalation of the oligomer or polymer) as described in U.S. Pat. Nos. 5,880,197 and 5,877,248, as well as by acidification with substitution with hydrogen (ion-exchanging the interlayer cations with hydrogen by use of an acid or ion-exchange resin) as described in U.S. Pat. Nos. 5,102,948 and 5,853,886.

C. Other Components

In addition to the components noted above, other additives may also be incorporated into the film of the present invention, such as compatibilizers, slip additives, melt stabilizers, processing stabilizers, heat stabilizers, light stabilizers, antioxidants, heat aging stabilizers, whitening agents, bonding agents, fillers, etc. Compatibilizers, for instance, may be employed in certain embodiments to help improve the affinity of the ethylene polymers to the nanoclay. When employed, compatibilizers may constitute from about 0.1 wt. % to about 10 wt. %, in some embodiments from about 0.2 wt. % to about 8 wt. %, and in some embodiments, from about 0.5 wt. % to about 5 wt. % of the polymer composition. One example of a suitable compatibilizer includes a polyolefin containing an olefin component and a polar component. The olefin component is non-polar and thus generally has an affinity for the ethylene polymer. The olefin component may generally be formed from any linear or branched α-olefin monomer, oligomer, or polymer (including copolymers) derived from an α-olefin monomer. In one particular embodiment, for example, the compatibilizer includes at least one linear or branched α-olefin monomer, such as those having from 2 to 20 carbon atoms and preferably from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin co-monomers are ethylene and propylene.

The polyolefin compatibilizer is also functionalized with a polar component, which can be grafted onto the polymer, incorporated as a monomeric constituent of the polymer (e.g., block or random copolymers), etc. When grafted onto a polymer backbone, particularly suitable polar groups are maleic anhydride, maleic acid, acrylic acid, methacrylic acid, fumaric acid, maleimide, maleic acid hydrazide, a reaction product of maleic anhydride and diamine, methylnadic anhydride, dichloromaleic anhydride, maleic acid amide, etc. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation FUSABOND®, such as the P Series (chemically modified polypropylene), E Series (chemically modified polyethylene), C Series (chemically modified ethylene vinyl acetate), A Series (chemically modified ethylene acrylate copolymers or terpolymers), M Series (chemically modified polyethylene), or N Series (chemically modified ethylene-propylene, ethylene-propylene diene monomer ("EPDM") or ethylene-octene). Alternatively, modifier polyolefins are also available from Chemtura Corp. under the designation POLYBOND® (e.g., acrylic acid-modified polypropylene) and Eastman Chemical Company under the designation Eastman G series.

As noted above, the polar component may also be incorporated into the polyolefin compatibilizer as a monomer. For example, a (meth)acrylic monomeric component may be employed in certain embodiments. As used herein, the term "(meth)acrylic" includes acrylic and methacrylic monomers, as well as salts or esters thereof, such as acrylate and methacrylate monomers. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof. Other types of suitable polar monomers include ester monomers, amide monomers, etc.

II. Film Construction

The film of the present invention may be mono- or multi-layered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers. In one embodiment, for example, it may be desirable to employ two skin layers that sandwich a base layer. Regardless of the particular construction, the skin and/or base layers may be formed from the polymer composition of the present invention. In one embodiment, for example, the base layer is formed from the polymer composition of the present invention and the skin layer(s) are formed from the polymer composition or from an additional polymer material. Likewise, in other possible embodiments, one or more of the skin layers are formed from the polymer composition of the present invention and the base layer is formed from an additional polymer material. When employed, the additional material may include any type of polymer, such as polyolefins (e.g., polyethylene, polypropylene, etc.), polyesters, polyamides, styrenic copolymers, polyurethanes, polyvinyl acetate, polyvinyl alcohol, etc.

When multiple layers are employed, the base layer typically constitutes a substantial portion of the weight of the film, such as from about 50 wt. % to about 99 wt. %, in some embodiments from about 55 wt. % to about 90 wt. %, and in some embodiments, from about 60 wt. % to about 85 wt. % of the film. The skin layer(s) may likewise constitute from about 1 wt. % to about 50 wt. %, in some embodiments from about 10 wt. % to about 45 wt. %, and in some embodiments, from about 15 wt. % to about 40 wt. % of the film. Each skin layer may also have a thickness of from about 0.1 to about 10 micrometers, in some embodiments from about 0.5 to about 5 micrometers, and in some embodiments, from about 1 to about 2.5 micrometers. Likewise, the base layer may have a thickness of from about from about 1 to about 40 micrometers, in some embodiments from about 2 to about 25 micrometers, and in some embodiments, from about 5 to about 20 micrometers. As noted above, the total thickness of the film is typically about 50 micrometers or less, in some embodiments from about 1 to about 40 micrometers, in some embodiments from about 5 to about 35 micrometers, and in some embodiments, from about 10 to about 30 micrometers.

Any of a variety of techniques may generally be employed to form the film of the present invention. In certain embodiments, for example, the components of the film (e.g., ethylene polymers, nanoclay, etc.) may be individually supplied to a film forming system and blended together as the film is being formed. In such cases, the nanoclay may be in the form of a powder containing particles, such as described above. Alternatively, however, it may be desirable to pre-blend the ethylene polymers and nanoclay to form a masterbatch, which is then subsequently supplied to the film forming system. Without intending to be limited by theory, it is believed such a multi-step process can allow the nanoclay to be more uniformly oriented, thereby even further enhancing ductility. When supplied, the nanoclay may itself be in the form of a masterbatch, which may contain nanoclay particles blended with a polymer (e.g., ethylene polymer), or in the form of a powder containing particles. For example, in one embodiment, a first masterbatch may be formed that contains the first and second ethylene polymers. Likewise, a second masterbatch may be formed that contains the nanoclay and optionally some portion of the first and/or second ethylene polymers.

Regardless of whether supplied individually or in the form of a masterbatch, the components can be melt blended together using any known extrusion device in the art. For example, a twin screw extruder may be employed that includes co-rotating screws rotatably mounted and received within a barrel (e.g., cylindrical barrel), which may be heated. The components are moved downstream from a feed end to a discharge end by forces exerted by rotation of the screws. The ratio of the length to outer diameter ("L/D") of the screws may be selected to achieve an optimum balance between throughput and blend uniformity. For example, too large of an L/D value may increase the retention time to such an extent that the nanoclay degrades beyond the desired level. On other hand, too low of an L/D value may not result in the desired degree of blending. Thus, the L/D value is typically from about 25 to about 60, in some embodiments from about 35 to about 55, and in some embodiments from about 40 to about 50. The speed of the screws may also be selected to achieve the desired residence time, shear rate, melt processing temperature, etc. Generally, an increase in product temperature is observed with increasing screw speed due to the additional mechanical energy input into the system. The frictional energy results from the shear exerted by the turning screw on the materials within the extruder and results in the fracturing of large molecules. This results in lowering the apparent viscosity and increasing the melt flow rate of the finished material. For example, the screw speed may range from about 50 to about 400 revolutions per minute ("rpm"), in some embodiments from about 100 to about 300 rpm, and in some embodiments, from about 120 to about 280 rpm. As a result, melt processing may occur at a temperature of from about 100° C. to about 500° C., in some embodiments, from about 150° C. to about 350° C., and in some embodiments, from about 150° C. to about 300° C. Typically, the apparent shear rate during melt processing may range from about 300 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows. Of course, other variables, such as the residence time during melt processing, which is inversely proportional to throughput rate, may also be controlled to achieve the desired blending.

Once formed, the pre-blended masterbatch may be supplied to a film-forming system. Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al. In yet another embodiment, however, the film is formed using a casting technique.

Figure 1:
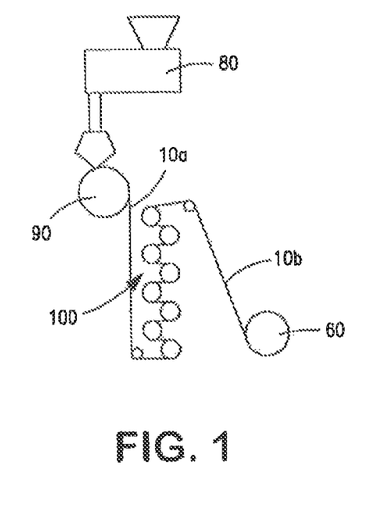
FIG. 1 is a schematic illustration of one embodiment of a process that can be used to form the film of the present invention.

Referring to FIG. 1, for instance, one embodiment of a method for forming a cast film is shown. In this embodiment, the pre-blended masterbatch is supplied to an extruder 80 for melt processing. To help achieve good alignment and orientation of the nanoclay, it is typically desired to use a single screw extruder during film formation. Such single screw extruders are typically divided into three sections along the length of the screw. The first section is a feed section where the solid material is introduced to the screw. The second section is a melting section where a majority of the melting of the solid occurs. Within this section, the screw generally possesses a tapered diameter to enhance melting of the polymer. The third section is the mixing section, which delivers the molten material in a constant amount for extrusion. The L/D ratio for the screw is typically from about 5 to about 50, in some embodiments from about 10 to about 40, and in some embodiments from about 15 to about 35. Such L/D ratios may be readily achieved in a single screw extruder by using mixing section(s) that constitute only a small portion of the length of the screw. The screw speed may likewise range from about 5 to about 150 rpm, in some embodiments from about 10 to about 100 rpm, and in some embodiments, from about 20 to about 80 rpm. As a result, melt processing may occur at a temperature of from about 100° C. to about 500° C., in some embodiments, from about 150° C. to about 350° C., and in some embodiments, from about 150° C. to about 300° C.

Once formed, the extruded material may be immediately chilled and cut into pellet form. In the embodiment of FIG. 1, the extruded material is cast onto a casting roll 90 to form a single-layered precursor film 10a. If a multilayered film is to be produced, the multiple layers are co-extruded together onto the casting roll 90. The casting roll 90 may optionally be provided with embossing elements to impart a pattern to the film. Typically, the casting roll 90 is kept at temperature sufficient to solidify and quench the sheet 10a as it is formed, such as from about 20 to 60° C. If desired, a vacuum box may be positioned adjacent to the casting roll 90 to help keep the precursor film 10a close to the surface of the roll 90. Additionally, air knives or electrostatic pinners may help force the precursor film 10a against the surface of the casting roll 90 as it moves around a spinning roll. An air knife is a device known in the art that focuses a stream of air at a very high flow rate to pin the edges of the film.

Once cast, the film 10a may then be optionally oriented in one or more directions to further improve film uniformity and reduce thickness. In the case of sequential orientation, the "softened" film is drawn by rolls rotating at different speeds of rotation such that the sheet is stretched to the desired draw ratio in the longitudinal direction (machine direction). If desired, the uniaxially oriented film may also be oriented in the cross-machine direction to form a "biaxially oriented" film. For example, the film may be clamped at its lateral edges by chain clips and conveyed into a tenter oven. In the tenter oven, the film may be reheated and drawn in the cross-machine direction to the desired draw ratio by chain clips diverged in their forward travel.

Referring again to FIG. 1, for instance, one method for forming a uniaxially oriented film is shown. As illustrated, the precursor film 10a is directed to a film-orientation unit 100 or machine direction orienter ("MDO"), such as commercially available from Marshall and Williams, Co. of Providence, R.I. The MDO has a plurality of stretching rolls (such as from 5 to 8) which progressively stretch and thin the film in the machine direction, which is the direction of travel of the film through the process as shown in FIG. 1. While the MDO 100 is illustrated with eight rolls, it should be understood that the number of rolls may be higher or lower, depending on the level of stretch that is desired and the degrees of stretching between each roll. The film may be stretched in either single or multiple discrete stretching operations. It should be noted that some of the rolls in an MDO apparatus may not be operating at progressively higher speeds. If desired, some of the rolls of the MDO 100 may act as preheat rolls. If present, these first few rolls heat the film 10a above room temperature. The progressively faster speeds of adjacent rolls in the MDO act to stretch the film 10a. The rate at which the stretch rolls rotate determines the amount of stretch in the film and final film weight. The resulting film 10b may then be wound and stored on a take-up roll 60. While not shown here, various additional potential processing and/or finishing steps known in the art, such as slitting, treating, aperturing, printing graphics, or lamination of the film with other layers (e.g., nonwoven web materials), may be performed without departing from the spirit and scope of the invention.

III. Laminates

Although by no means required, it may be desirable in certain cases to laminate an additional material to the nanocomposite of the film of the present invention, such as fibrous webs (e.g., nonwoven webs), other films, foams, strands, etc. For example, when employed as a backsheet in an absorbent article, the film may be laminated to a nonwoven facing that reduces the coefficient of friction and enhances the cloth-like feel of the laminate surface. Exemplary polymers for use in forming nonwoven web materials may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, biodegradable polymers, such as those described above, may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives, such as processing aids or treatment compositions to impart desired properties to the fibers, residual amounts of solvents, pigments or colorants, and so forth. If desired, the nonwoven facing used to form the laminate may itself have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al. The basis weight of the nonwoven facing may generally vary, such as from about 5 grams per square meter ("gsm") to 120 gsm, in some embodiments from about 10 gsm to about 70 gsm, and in some embodiments, from about 15 gsm to about 35 gsm. When multiple nonwoven web materials, such materials may have the same or different basis weights.

IV. Absorbent Article

The nanocomposite film of the present invention may be used in a wide variety of absorbent articles. An "absorbent article" generally refers to any article capable of absorbing water or other fluids. Examples of some absorbent articles include, but are not limited to, personal care absorbent articles, such as diapers, training pants, absorbent underpants, incontinence articles, feminine care articles (e.g., sanitary napkins, pantiliners, etc.), swim wear, baby wipes, and so forth; medical absorbent articles, such as garments, fenestration materials, underpads, bedpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al. Materials and processes suitable for forming such absorbent articles are well known to those skilled in the art. Typically, absorbent articles include a generally liquid-impermeable layer (e.g., backsheet), a liquid-permeable layer (e.g., topsheet, surge layer, etc.), and an absorbent core. The nanocomposite film of the present invention, or a laminate thereof, may be used to form any component of the article, such as the backsheet and/or topsheet. In one particular embodiment, the film is employed in the backsheet. Alternatively, the nanocomposite film may be used in other components of the article, such as wing portions that laterally extend from a side region of the article.

Figure 2:
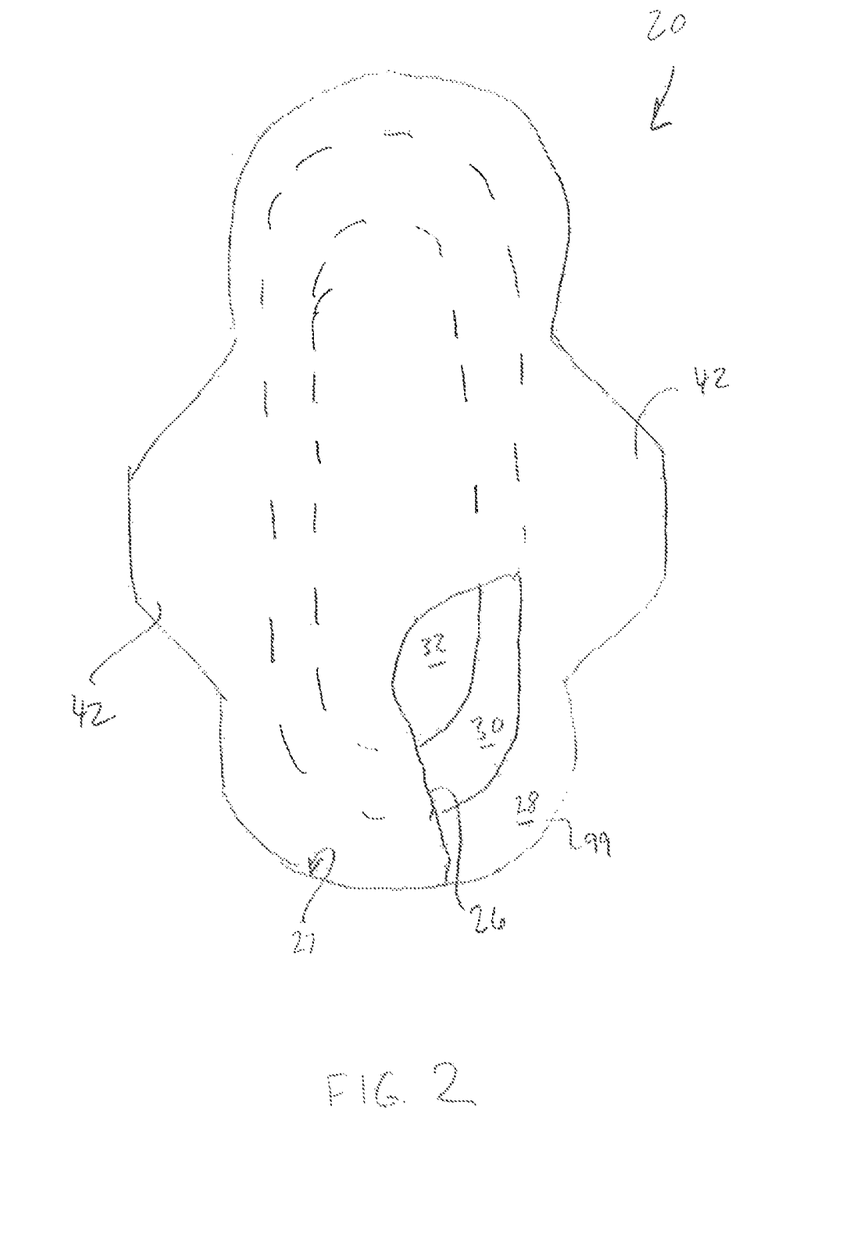
FIG. 2 is a top view of one embodiment of the absorbent article of the present invention.

Various embodiments of an absorbent article that may be formed according to the present invention will now be described in more detail. Referring to FIG. 2, for instance, one embodiment of a one particular embodiment of the feminine care absorbent article 20 of the present invention will now be described in more detail. As shown, the feminine care absorbent article 20 (e.g., feminine care pad or napkin) includes a topsheet 26, a backsheet 28, and an absorbent core 30 positioned between the topsheet 26 and the backsheet 28. In certain embodiments, the topsheet 26 and/or backsheet 28 may contain the nanocomposite film of the present invention. The topsheet 26 defines a body-facing surface 27 of the absorbent article 20. The absorbent core 30 is positioned inwardly from the outer periphery of the absorbent article 20 and includes a body-facing side positioned adjacent the topsheet 26 and a garment-facing surface positioned adjacent the backsheet 28. Typically, the topsheet 26 and the backsheet 28 are joined by adhesive bonding, ultrasonic bonding, or any other suitable joining method known in the art, the sealed edges defining an overall sealed peripheral edge 99 of the article 20. The article 20 may take on various geometries but will generally have opposite lateral sides and longitudinal ends.

The topsheet 26 is generally designed to contact the body of the user and is liquid-permeable. The liquid permeable topsheet 26 has an outwardly facing surface that may contact the body of the wearer and receive aqueous fluids from the body. The topsheet 26 is provided for comfort and conformability and functions to direct bodily exudates away from the body, through the topsheet 26 and toward the absorbent core 30. The topsheet 26 retains little or no liquid in its structure so that it provides a relatively comfortable and non-irritating surface next to the tissues within the vestibule of a female wearer. In certain embodiments, the topsheet 26 may contain the nanocomposite film of the present invention. The topsheet 26 may also contain a woven or nonwoven material that is easily penetrated by bodily exudates contacting the surface of the baffle. Examples of suitable materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. A specific example of a suitable topsheet material is a bonded carded web made of polypropylene and polyethylene such as that used as topsheet stock for KOTEX® pantiliners. The topsheet 26 may also contain a plurality of apertures (not shown) formed therethrough to permit body fluid to pass more readily into the absorbent core 30. The apertures may be randomly or uniformly arranged throughout the topsheet 26, or they may be located only in the narrow longitudinal band or strip arranged along the longitudinal axis of the absorbent article 20. The apertures permit rapid penetration of body fluid down into the absorbent core 30. The size, shape, diameter and number of apertures may be varied to suit one's particular needs.

The backsheet 28 is generally liquid-impermeable and designed to face the inner surface, i.e., the crotch portion of an undergarment (not shown). The backsheet 28 may permit a passage of air or vapor out of the absorbent article 20, while still blocking the passage of liquids. Any liquid-impermeable material may generally be utilized to form the backsheet 28. In certain embodiments, the backsheet 28 may contain the nanocomposite film of the present invention. Alternatively, the backsheet 28 may contain a conventional polyolefin film, such as a polyethylene film such as that used in KOTEX® pantiliners.

As indicated above, an absorbent core 30 is positioned between the topsheet 26 and the backsheet 28 that provides capacity to absorb and retain bodily exudates. The absorbent core 30 may be formed from a variety of different materials and contain any number of desired layers. For example, the core 30 typically includes one or more layers of an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material includes a matrix of cellulosic fluff, and may also include superabsorbent material. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

The topsheet 26 may be maintained in secured relation with the absorbent core 30 by bonding all or a portion of the adjacent surfaces to one another. A variety of bonding mechanisms known to one of skill in the art may be utilized to achieve any such secured relation. Examples of such mechanisms include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent. The topsheet 26 typically extends over the upper, bodyside surface of the absorbent core 30, but can alternatively extend around the article to partially or entirely, surround or enclose the absorbent core. Alternatively, the topsheet 26 and the backsheet 28 can have peripheral margins that extend outwardly beyond the terminal, peripheral edges of the absorbent core 30, and the extending margins can be joined together to partially or entirely, surround or enclose the absorbent core.

Although not required, the absorbent article 20 may also contain other additional layers as is known in the art, any of which may contain the nanocomposite film of the present invention if so desired. In FIG. 2, for example, a liquid-permeable intake layer 32 is positioned vertically between the topsheet 26 and the absorbent core 30. The intake layer 32 may be made of a material that is capable of rapidly transferring, in the z-direction, body fluid that is delivered to the topsheet 26. The intake layer 32 may generally have any shape and/or size desired. In one embodiment, the intake layer 32 has a rectangular shape, with a length equal to or less than the overall length of the absorbent article 20, and a width less than the width of the absorbent article 20. For example, a length of between about 150 mm to about 300 mm and a width of between about 10 mm to about 60 mm may be utilized. Any of a variety of different materials are capable of being used for the intake layer 32 to accomplish the above-mentioned functions. The material may be synthetic, cellulosic, or a combination of synthetic and cellulosic materials. For example, airlaid cellulosic tissues may be suitable for use in the intake layer 32. The airlaid cellulosic tissue may have a basis weight ranging from about 10 grams per square meter (gsm) to about 300 gsm, and in some embodiments, between about 40 gsm to about 150 gsm. The airlaid tissue may be formed from hardwood and/or softwood fibers. The airlaid tissue has a fine pore structure and provides an excellent wicking capacity, especially for menses.

The absorbent article 20 may also contain a transfer delay layer (not shown) positioned between the intake layer 32 and the absorbent core 30. The transfer delay layer may contain a material that is substantially hydrophobic, such as a nonwoven web composed of polypropylene, polyethylene, polyester, etc. One example of a material suitable for the transfer delay layer is a spunbond web composed of polypropylene, multi-lobal fibers. Further examples of suitable transfer delay layer materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer 36 are described in U.S. Pat. No. 4,798,603 to Meyer, et al. and U.S. Pat. No. 5,248,309 to Serbiak, et al. To adjust performance, the transfer delay layer may also be treated with a selected amount of surfactant to increase its initial wettability. The transfer delay layer typically has a basis weight less than that of the other absorbent members. For example, the basis weight of the transfer delay layer 36 is typically less than about 250 grams per square meter (gsm), and in some embodiments, between about 40 gsm to about 200 gsm.

The absorbent article 20 may also include laterally extending wing portions 42 that may be integrally connected to side regions along the intermediate portion of the article. As noted above, the nanocomposite film of the present invention may be particularly suitable for forming the wing portions 42 due to its enhanced stiffness. In this regard, the wing portions 42 may be a separately provided material that is subsequently attached or otherwise operatively joined to the intermediate portion of the article. In other configurations, the wing portions 42 may be unitarily formed with one or more components of the article. As representatively shown in FIG. 1, for example, either or both wing portions 42 may be formed from a corresponding, operative extension of the material employed to form the topsheet 26. In such embodiments, the nanocomposite film of the present invention may be used in both the topsheet 26 and the wing portions 42. Alternatively, either or both wing portions 42 may be formed from a corresponding, operative extension of the material employed to form the backsheet 28. In such embodiments, the nanocomposite film of the present invention may be used in both the backsheet 28 and the wing portions 42.

Although various configurations of a feminine care article have been described above, it should be understood that other configurations are also included within the scope of the present invention. In addition, the present invention is by no means limited to feminine care articles. In fact, any other absorbent article may be formed in accordance with the present invention, including, but not limited to, other personal care absorbent articles, such as training pants, absorbent underpants, adult incontinence products, diapers, swim wear, baby wipes, and so forth; medical absorbent articles, such as garments, fenestration materials, underpads, bandages, absorbent drapes, and medical wipes; food service wipers; clothing articles; and so forth. The film may also be used in applications other than absorbent articles. For example, the film may be employed as an individual wrap, packaging pouch, or bag for the disposal of a variety of articles, such as food products, absorbent articles, etc. Various suitable pouch, wrap, or bag configurations for absorbent articles are disclosed, for instance, in U.S. Pat. No. 6,716,203 to Sorebo, et al. and U.S. Pat. No. 6,380,445 to Moder, et al., as well as U.S. Patent Application Publication No. 2003/0116462 to Sorebo, et al.

The present invention may be better understood with reference to the following examples.

Test Methods

Mechanical Properties:

The strip tensile strength values were determined in substantial accordance with ASTM Standard D638-99. A constant-rate-of-extension type of tensile tester was employed. The tensile testing system was an MTS Synergy 200 tensile frame. The tensile tester was equipped with TESTWORKS 4.08B software from MTS Corporation to support the testing. The load cell was 100 Newtons. The film samples were initially cut into dog-bone shapes with a center width of 3.0 mm before testing. The samples were held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run using a gauge length of 18.0 millimeters and a break sensitivity of 40%. Five samples were tested by applying the test load along the machine-direction and five samples were tested by applying the test load along the cross direction. During the test, samples were stretched at a crosshead speed of about 127 millimeters per minute until breakage occurred. The modulus, peak stress, peak elongation (percent strain at break), and energy per volume at break were measured in the machine direction ("MD") and cross-machine directions ("CD").

Noise Level:

Noise levels of film and absorbent article samples may be tested in an apparatus comprised of a test chamber, a control chamber, and a sound level meter. The purpose of the apparatus is to manipulate an article in a controlled noise environment, and to accurately quantify the noise produced by the movement of the sample. In general terms, a sample is physically deformed within the test apparatus to generate a noise level. As used herein, the "noise level" refers to the equivalent continuous noise level (referred to as "$L_{EQ}$" or "$L_{AT}$"), which is the time average sound level (expressed in units of dB) as determined according to the following equation:

$$L_{eq} = 10 \log \left[ \frac{1}{t_2 - t_1} \int_{t_1}^{t_2} \frac{p_A^2}{p_0^2} dt \right]$$

$p_0$ is a reference pressure level (typically 20 µPa);
$p_A$ is the acquired sound pressure;
t is time;
$t_1$ is the start time for measurement; and
$t_2$ is the end time for measurement.

This value is also described in IEC 61672-1 (2013).

Figure 3:
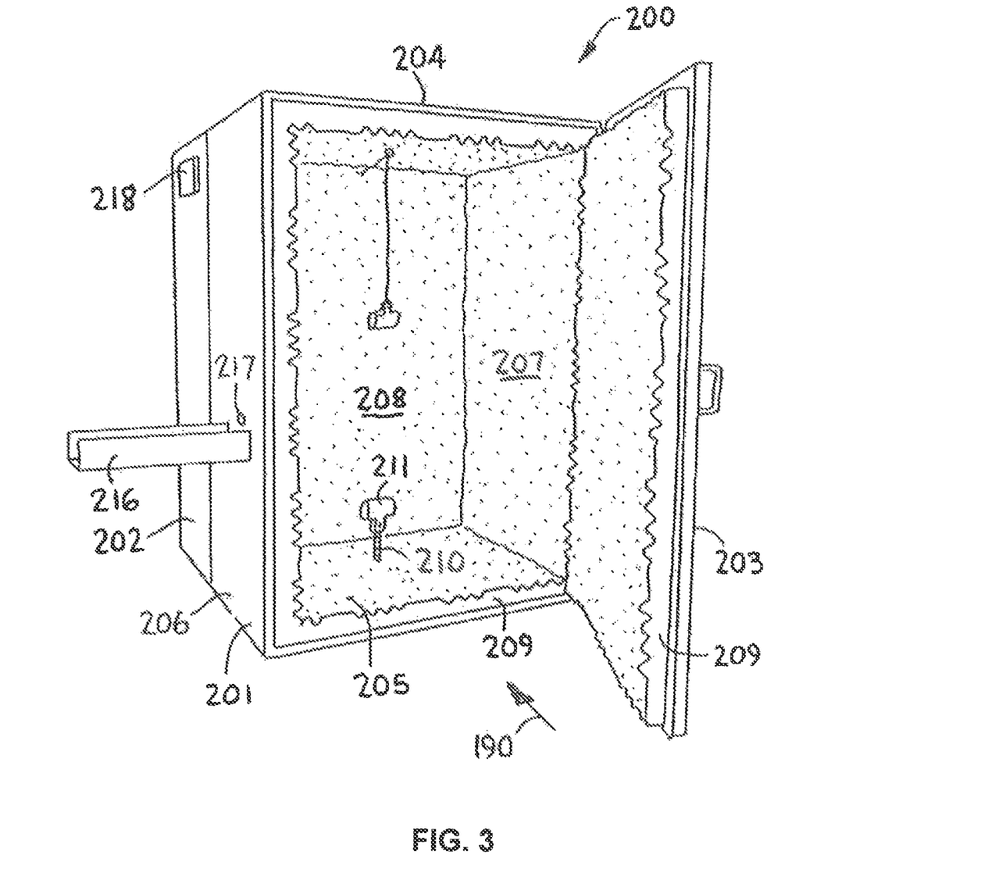
FIG. 3 is a perspective view of a testing apparatus that may be used to evaluate noise levels, with the apparatus door open.
Figure 4:
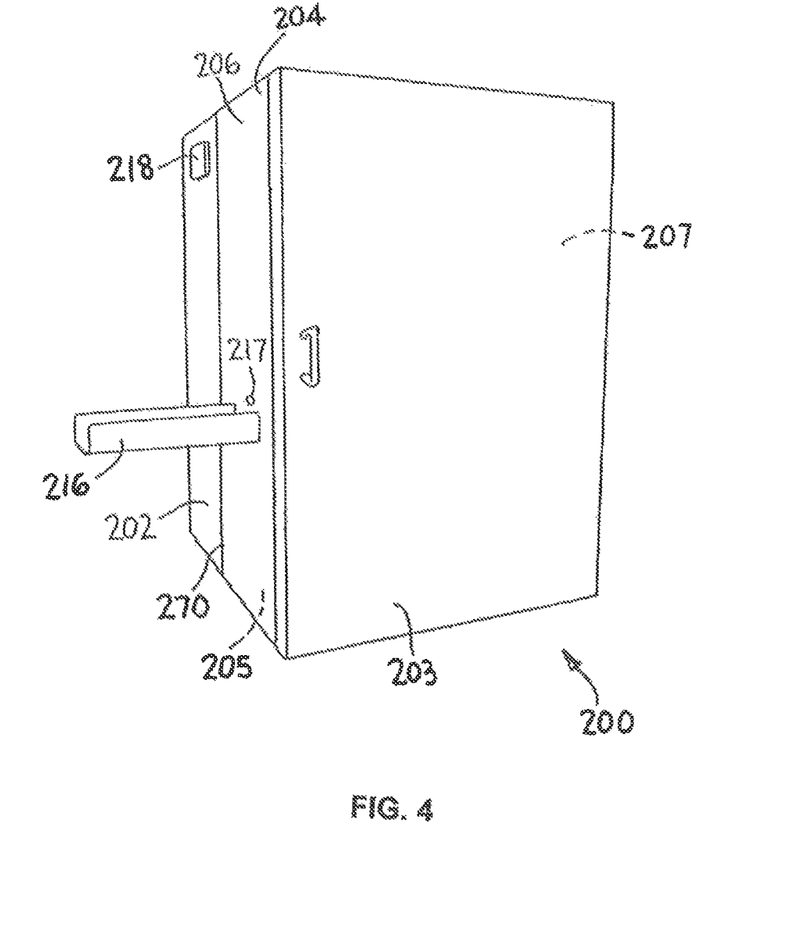
FIG. 4 is a perspective view of the testing apparatus of FIG. 3, with the apparatus door closed.
Figure 5:
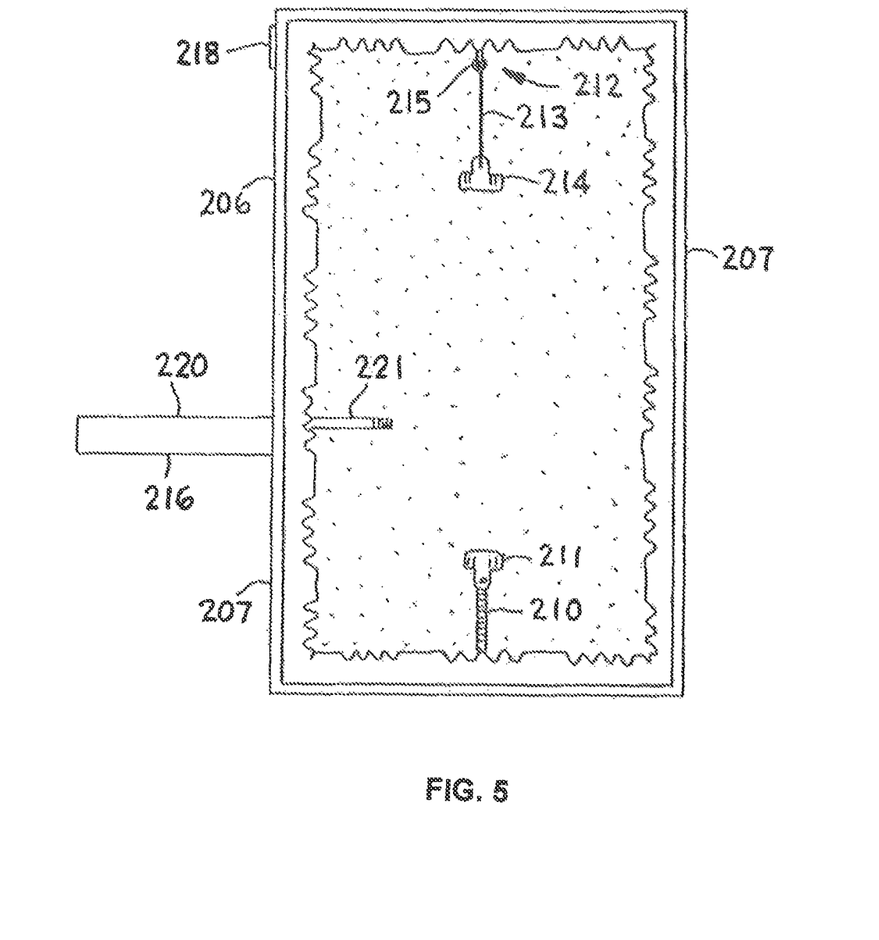
FIG. 5 is a plan view of the apparatus of FIG. 3 taken along arrow 190.

The testing apparatus is illustrated in FIGS. 3-5. The testing apparatus 200 includes a test chamber 201 and a control chamber 202. The test chamber 201 includes a door 203, a top wall 204, a bottom wall 205, two side walls 206 and 207, and a rear wall 208. The door and each wall are constructed of 0.25-inch (0.635 cm) thick 6061 grade anodized aluminum. The door 203 and rear wall 208 are each 36 inches (91.4 cm) in height and 24 inches (61.0 cm) in width. The test chamber side walls 206 and 207 are each 36 inches (91.4 cm) high and 18 inches (45.7 cm) wide. The test chamber top and bottom panels are each 24 inches wide (61.0 cm) and 18 inches (45.7 cm) long. The interior surface of the door 203 and each wall 204-208 has applied thereto two-inch thick polyurethane sound-dampening foam 209, available from Illbruck Inc. under the brand name SONEX and stock number SOC-2. As shown, a sound level meter support 216 extends perpendicularly outward from side wall 206 just below a microphone orifice 217. The microphone orifice 217 is positioned 14.5 centimeters above the floor of the bottom wall 205, and is further centered between the door 203 and the rear wall 208. The sound level meter support 216 is constructed of aluminum and is bolted (not shown) to side wall 206. The control chamber 202 includes a front wall 230, two side walls 231 and 232, a top wall 233, and a bottom wall 234. Each wall is constructed of 0.125-inch (0.3175 cm) thick 6061 grade anodized aluminum. The front wall 230 is 36 inches (91.4 cm) high and 24 inches (61.0 cm) wide. The control chamber side walls 231 and 232 are each 36 inches high (91.4 cm) and 12 inches (30.5 cm) wide. The control chamber top and bottom walls 233 and 234 are each 24 inches (61.0 cm) wide and 12 inches (30.5 cm) long. The control chamber 202 is bolted (not shown) to the outer surface of rear wall 208 along seam 270 (FIG. 4). The outer surface of the rear wall 208, and the front wall 230, two side walls 231 and 232, top wall 233, and bottom wall 234 of the control chamber 202 are each coated with 0.600-inch (1.524 cm) thick sound insulating material, part number NYC-600BE, available from Small Parts, Inc. The testing apparatus 200 further includes a sound level meter 220 (FIG. 5), such as a model 1900, equipped with a model OB-100 octave filter set, both available from Quest Technologies, a company having offices in Oconomowoc, Wis. The sound level meter is supported by a model QC-20 calibrator and QuestSuite master module software, each also available from Quest Technologies. The software is installed on a personal computer (not shown). During operation of the testing apparatus, the sound level meter 220 rests in the sound level meter support 216. The sound level meter includes a microphone 221 extending 4.75 inches (12 centimeters) therefrom.

Although by no means required, the apparatus may also contain features for automatically deforming a sample during a test. For example, the apparatus may contain a lower slide bracket 210, a six-inch (15.24 cm) high Series A1500 Model available from Velmex, Inc., which extends from the bottom wall 205 into the test chamber 201, and a lower clamp 211 that is affixed to the lower slide bracket 210. An eyelet 212 (FIG. 5) may optionally extend from the top wall 204 into the test chamber 201, and an optional lanyard 213 extends through the eyelet 212. One end of the lanyard 213 extends into the test chamber 201, and has an upper clamp 214 affixed thereto. The other end of the lanyard 213 extends into the control chamber 202 through a lanyard orifice 215, which is ⅝ inch (16 mm) in diameter. The lanyard may be a premium-braid, 80-lb test Spiderwire®, part number SB80G-300, manufactured by Johnson Worldwide Associates (JWA), Inc.

Prior to testing a specimen using the testing apparatus 200, the following steps are followed:

1. Calibrate the sound level meter 220 following the instructions in the manufacturer's manual.
2. Insert the full length of the microphone 221 into the testing chamber 201 (it should extend past the wall and sound dampening material approximately 2.5 inches (6.35 cm)), positioned at a 90-degree angle to side wall 206. Allow the sound level meter 220 to rest in the sound level meter support 216.
3. Activate the sound level meter per the manufacturer's instruction manual. This will collect the ambient noise inside the cavity of the test chamber 200.
4. Set the octave filter to 2,000 or 4,000 Hz and take a reading for each test conducted by activating the sound level meter until the testing has been completed.

Having calibrated the testing apparatus 200 and having identified the ambient noise, five (5) specimens of a sample (film or absorbent article) may then be physically deformed approximately 15 to 20 centimeters from the microphone within the test apparatus.

The film samples in the Examples below were manually deformed as follows:

1. Open the dominant hand with the palm facing upward;
2. Place the film sample in the palm of the dominant hand;
3. Compress the test specimen by making a gentle fist;
4. Quickly open the hand and release the test specimen; and
5. Repeat this four (4) more times to equate to five (5) film "crumples."

Regardless of the manner of physical deformation, the tests ranged between 1 to 2 seconds in duration. All tests involved starting the sound level meter, completing the respective product manipulation, and then stopping the sound level meter. The chamber door was allowed to remain open during testing to accommodate the arms and hands of the tester, as well as the motions of the product manipulation protocols. The ambient noise outside of the apparatus was quiet and was the same during calibration (including measuring the ambient noise level) and testing of the sample.

Control 1

A film was formed from Dowlex™ EG 2244G using a HAAKE Rheomex® 252p single screw extruder and a 6" cast film die. Dowlex™ EG2244G is a linear low density polyethylene having a melt flow index of 1.0 g/10 minutes at 190° C. (Dow Chemical). The screw had a diameter of 19.05 mm and an L/D of 25 (L is the screw length). A chill roll was used to cool and flatten the polymer as it exited the cast film die. The screw speed was maintained at 38 rpm for a target thickness of 12.7 micrometers. The four controlled temperature zones from the first heating zone to the die adaptor were set at 180° C., 180° C., 180° C., and 180° C., respectively. The torque on the extruder was 24 N-m and the pressure at the die was 520 psi.

Control 2

A film was formed from DPDA-3320 N7 using a HAAKE Rheomex® 252p single screw extruder and a 6" cast film die. DPDA-3320 N7 is a high density polyethylene having a melt flow index of 2.0 g/10 minutes at 190° C. (Dow Chemical). The screw had a diameter of 19.05 mm and an L/D of 25 (L is the screw length). A chill roll was used to cool and flatten the polymer as it exited the cast film die. The screw speed was maintained at 40 rpm for a target thickness of 12.7 micrometers. The four controlled temperature zones from the first heating zone to the die adaptor were set at 170° C., 180° C., 185° C., and 190° C., respectively. The torque on the extruder was 20 N-m and the pressure at the die was 493 psi.

EXAMPLE 1

A film was formed from 90 wt.% of a first masterbatch and 10 wt.% of a second masterbatch. The first masterbatch was formed by dry blending 80 wt.% Dowlex™ 2244G (LLDPE) and 20 wt.% DPDA-3320 N7 (HDPE) and the second masterbatch was formed by dry blending 80 wt.% NanoMax™ LDPE (Nanocor, Inc.) and 20 wt.% NanoMax™ HDPE (Nanocor, Inc.). NanoMax™ LDPE contains 50wt.% Nanomer™ nanoclay (quaternary ammonium surface-modified montmorillonite) and 50 wt.% of LDPE and maleic anhydride grafted LDPE, and NanoMax™ HDPE contains 50 wt.% Nanomer™ nanoclay and 50 wt.% HDPE and maleic anhydride grafted HDPE. The materials were delivered through two K-Tron gravimetric feeders and melt blended together using a Werner & Pfleiderer (W&P) ZSK-30 co-rotating, twin screw extruder. The extruder had 14 processing barrels, with 13 heated barrels. Three barrels are open barrels. The outer diameters of the screws were 30 mm and the inner screw diameters were 21.3 mm, The lengths of the screws were 1328 mm and the total processing section length was 1338 mm. The zones had a processing temperature of 171° C., 181° C., 188° C., 190° C., 191° C., 195° C., and 200° C., respectively. The melt temperature was about 224° C. and the pressure was about 260-290 psi. The compounding speed in the twin screw extruder was set as 250 rpm.

Once formed, the blends were formed into a film using a HAAKE single screw extruder as described in Control 1. The screw speed was maintained at 35 rpm for a target thickness of 12.7 micrometers. The four controlled temperature zones from the first heating zone to the die adaptor were set at 190° C., 200° C., 200° C., and 200° C., respectively. The torque on the extruder was 12 N-m and the pressure at the die was 406 psi.

EXAMPLE 2

A film was formed from 90 wt. % of a first masterbatch and 10 wt. % of a second masterbatch. The first masterbatch was formed by dry blending 60 wt. % Dowlex™ 2244G (LLDPE) and 40 wt. % DPDA-3320 N7 (HDPE) and the second masterbatch was formed by dry blending 60 wt. % NanoMax™ LDPE and 40 wt. % NanoMax™ HDPE. The materials were delivered through two K-Tron gravimetric feeders and melt blended together using a Werner & Pfleiderer (W&P) ZSK-30 co-rotating, twin screw extruder as described in Example 1. The zones had a processing temperature of 166° C., 183° C., 191° C., 190° C., 191° C., 195° C., and 201° C., respectively. The melt temperature was about 227° C. and the pressure was about 220-340 psi. The compounding speed in the twin screw extruder was set as 250 rpm. Once formed, the blends were formed into a film using a HAAKE single screw extruder as described in Control 1. The screw speed was maintained at 33 rpm for a target thickness of 12.7 micrometers. The four controlled temperature zones from the first heating zone to the die adaptor were set at 190° C., 200° C., 200° C., and 200° C., respectively. The torque on the extruder was 14 N-m and the pressure at the die was 406 psi.

EXAMPLE 3

A film was formed from 90 wt. % of a first masterbatch and 10 wt. % of a second masterbatch. The first masterbatch was formed by dry blending 40 wt. % Dowlex™ 2244G (LLDPE) and 60 wt. % DPDA-3320 N7 (HDPE) and the second masterbatch was formed by dry blending 40 wt. % NanoMax™ LDPE and 60 wt. % NanoMax™ HDPE. The materials were delivered through two K-Tron gravimetric feeders and melt blended together using a Werner & Pfleiderer (W&P) ZSK-30 co-rotating, twin screw extruder as described in Example 1. The zones had a processing temperature of 169° C., 177° C., 191° C., 191° C., 190° C., 195° C., and 200° C., respectively. The melt temperature was about 225° C. and the pressure was about 280-320 psi. The compounding speed in the twin screw extruder was set as 250 rpm. Once formed, the blends were formed into a film using a HAAKE single screw extruder as described in Control 1. The screw speed was maintained at 35 rpm for a target thickness of 12.7 micrometers. The four controlled temperature zones from the first heating zone to the die adaptor were set at 190° C., 200° C., 200° C., and 200° C., respectively. The torque on the extruder was 16 N-m and the pressure at the die was 435 psi.

EXAMPLE 4

A film was formed from 90 wt. % of a first masterbatch and 10 wt. % of a second masterbatch. The first masterbatch was formed by dry blending 20 wt. % Dowlex™ 2244G (LLDPE) and 80 wt. % DPDA-3320 N7 (HDPE) and the second masterbatch was formed by dry blending 20 wt. % NanoMax™ LDPE and 80 wt. % NanoMax™ HDPE. The materials were delivered through two K-Tron gravimetric feeders and melt blended together using a Werner & Pfleiderer (W&P) ZSK-30 co-rotating, twin screw extruder as described in Example 1. The zones had a processing temperature of 170° C., 180° C., 190° C., 191° C., 190° C., 195° C., and 200° C., respectively. The melt temperature was about 226° C. and the pressure was about 280-320 psi. The compounding speed in the twin screw extruder was set as 250 rpm. Once formed, the blends were formed into a film using a HAAKE single screw extruder as described in Control 1. The screw speed was maintained at 35 rpm for a target thickness of 12.7 micrometers. The four controlled temperature zones from the first heating zone to the die adaptor were set at 190° C., 200° C., 200° C., and 200° C., respectively. The torque on the extruder was 16 N-m and the pressure at the die was 420 psi.

The films of Examples 1-4 were then conditioned overnight at 23±2° C. and 50±5% RH and subjected to mechanical testing as described above. The results are set forth below in Table 1.

TABLE 1

Mechanical Properties

| Ex. | LLDPE (wt. %) | LDPE (wt. %) | HDPE (wt. %) | Wt. Ratio of (LLDPE + LDPE)/HDPE | Nanoclay (wt. %) | Avg. Peak Stress (MPa) | | Avg. Peak Elongation (%) | | Avg. Modulus (MPa) | | Avg. Energy Per Volume at Break (J/cm$^3$) | |
|---|---|---|---|---|---|---|---|---|---|---|---|---|---|
| | | | | | | MD | CD | MD | CD | MD | CD | MD | CD |
| 1 | 72 | 4 | 19 | 4.0 | 5 | 52 | 28 | 340 | 850 | 230 | 210 | 93 | 126 |
| 2 | 54 | 3 | 38 | 1.5 | 5 | 55 | 29 | 330 | 900 | 280 | 280 | 98 | 147 |
| 3 | 36 | 2 | 57 | 0.7 | 5 | 52 | 29 | 320 | 930 | 320 | 340 | 93 | 158 |
| 4 | 18 | 1 | 76 | 0.3 | 5 | 56 | 28 | 350 | 900 | 410 | 500 | 107 | 157 |

As indicated, the mechanical properties (e.g., modulus) generally improved with the incorporation of nanoclay.

Control 3

A commercial film was tested that is produced by Quanxing Plastics, Inc. The film had a basis weight of 18 grams per square meters and was cast extruded from a blend containing 35 to 45 wt. % high density polyethylene (HDPE 5070), 20 to 30 wt. % low density polyethylene (LDPE LD100AC), 25 to 35 wt. % linear low density polyethylene (LLDPE 7050), and 5 to 10 wt. % of a titanium dioxide masterbatch (1605H). A micro-embossed pattern having a depth of 1 to 5 micrometers was formed on a surface of the film.

EXAMPLE 5

A film was formed from a blend containing 93.5 wt. % of a polyethylene masterbatch, 4.5 wt. % of Clayton™ HY, and 2 wt. % of Fusabond® E-528, which is a graft copolymer of polyethylene and maleic anhydride available from DuPont. The polyethylene masterbatch contained 35 to 45 wt. % high density polyethylene (HDPE 5070), 20 to 30 wt. % low density polyethylene (LDPE LD100AC), 25 to 35 wt. % linear low density polyethylene (LLDPE 7050), and 5 to 10 wt. % of a titanium dioxide masterbatch (1605H). Clayton™ HY is an organoclay powder treated with quaternary ammonium solution and is available from BYK Additives, Inc. (Gonzales Tex.). The blend was formed using a co-rotating, twin screw extruder available from Entek®. The extruder had 14 processing barrels, with 13 heated barrels. Three barrels are open barrels. The outer diameter of the screws was 53 mm. The processing temperatures along the extruder were set as 175° C. and the compounding speed in the twin extruder was set as 700 rpm. The resultant strands were cooled in a water bath with 15 feet length in total. The cooled strand was then pelletized and collected for the following film processing.

A film was thereafter produced from the resulting blend using a single-screw extruder. The extruder has 8 processing barrels, with 7 heated barrels with temperatures ranging from 175-210° C. The screw speed was adjusted between 66.5 and 68.6 rpm depending on the required film thickness. The corresponding line speed was adjusted between 85 and 90 meters per minute. The resulting film had a basis weight of 13.5 grams per square meter. A micro-embossed pattern having a depth of 1 to 5 micrometers was formed on a surface of the film.

EXAMPLE 6

A film was formed as described in Example 5 except that a deep embossing pattern having a depth of 5 to 15 micrometers was formed on the surface.

The films of Control 3, Example 5, and Example 6 were then tested for noise level as described herein. The tested films were rectangular and had a size of 13.5 centimeters by 28.0 centimeters. The results are shown in Table 2 below.

TABLE 2

Noise Level of Films at 4,000 Hz

| | Noise Level (dB) | Normalized Noise Level |
|---|---|---|
| Control 3 | 46.0 | 2.6 |
| Example 5 | 39.6 | 2.2 |
| Example 6 | 38.0 | 2.1 |
| Ambient | 17.7 | — |

As indicated above, the film of Examples 5 and 6 showed considerable reduction in noise level compared with the control sample.

While the invention has been described in detail with respect to the specific embodiments thereof, it will be appreciated that those skilled in the art, upon attaining an understanding of the foregoing, may readily conceive of alterations to, variations of, and equivalents to these embodiments.

Accordingly, the scope of the present invention should be assessed as that of the appended claims and any equivalents thereto.

What is claimed is:

1. An absorbent article comprising
a liquid permeable layer, a generally liquid-impermeable layer, and an absorbent core positioned between the liquid permeable layer and the generally liquid-impermeable layer,
wherein the absorbent article contains a film having a thickness of 50 micrometers or less, the film containing a layer that is formed from a polymer composition, wherein the polymer composition contains
a first ethylene polymer having a density of 0.94 g/cm$^3$ or less,
a second ethylene polymer having a density of greater than 0.94 g/cm$^3$ and less than 0.98 g/cm$^3$, and
a nanoclay having an organic surface treatment,
wherein the weight ratio of the first ethylene polymer to the second ethylene polymer is from about 0.1 to about 10, and
wherein the film exhibits a Young's modulus in the machine direction of from about 150 to about 1000 Megapascals.

2. The absorbent article of claim 1, wherein ethylene polymers having a density of 0.94 g/cm$^3$ or less constitute from about 5 wt. % to about 90 wt. % of the polymer composition and ethylene polymers having a density of greater than about 0.94 g/cm³ and less than 0.98 g/cm³ constitute from about 5 wt. % to about 90 wt. % of the polymer composition.

3. The absorbent article of claim 1, wherein the nanoclay constitutes from about 0.5 wt. % to about 20 wt. % of the polymer composition.

4. The absorbent article of claim 1, wherein the first ethylene polymer, the second ethylene polymer, or both include a copolymer of ethylene and an α-olefin.

5. The absorbent article of claim 1, wherein the first ethylene polymer includes linear low density polyethylene, low density polyethylene, or a mixture thereof.

6. The absorbent article of claim 5, wherein the first ethylene polymer includes a mixture of linear low density polyethylene and low density polyethylene and wherein the low density polyethylene is present in an amount of from 1 wt. % to 4 wt. %.

7. The absorbent article of claim 1, wherein the second ethylene polymer includes high density polyethylene.

8. The absorbent article of claim 1, wherein the nanoclay includes a phyllosilicate.

9. The absorbent article of claim 8, wherein the phyllosilicate includes a montmorillonite or a salt thereof.

10. The absorbent article of claim 1, wherein the nanoclay includes platelets having an average thickness of from about 0.2 to about 100 nanometers.

11. The absorbent article of claim 1, wherein the organic surface treatment includes a quaternary onium.

12. The absorbent article of claim 1, wherein the polymer composition further comprises a polyolefin compatibilizer that includes an olefin component and a polar component.

13. The absorbent article of claim 12, wherein the polyolefin compatibilizer includes a carboxylic acid or carboxylic acid anhydride grafted polyolefin.

14. The absorbent article of claim 1, wherein the film exhibits a Young's modulus in the cross-machine direction of from about 200 to about 1200 Megapascals, or a combination thereof.

15. The absorbent article of claim 1, wherein the film exhibits a peak elongation in the machine direction of about 200% or more and an ultimate tensile strength in the machine direction of from about 15 to about 150 Megapascals.

16. The absorbent article of claim 1, wherein the film exhibits a peak elongation in the cross-machine direction of about 700% or more and an ultimate tensile strength in the cross-machine direction of from about 15 to about 150 Megapascals.

17. The absorbent article of claim 1, wherein absorbent article further comprises at least one wing that extends laterally from an edge of the article, wherein the wing contains the film.

18. The absorbent article of claim 1, wherein the generally liquid-impermeable layer is a backsheet of the absorbent article, the backsheet containing the film.

19. A film having a thickness of about 50 micrometers or less, wherein the film contains a layer that is formed from a polymer composition, the polymer composition containing
from about 5 wt. % to about 90 wt. % of a first ethylene polymer having a density of 0.94 g/cm³ or less,
from about 5 wt. % to about 90 wt. % of a second ethylene polymer having a density of greater than 0.94 g/cm³ and less than 0.98 g/cm³, and
from about 0.5 wt. % to about 20 wt. % of a nanoclay having an organic surface treatment,
wherein the weight ratio of the first ethylene polymer to the second ethylene polymer is from about 0.1 to about 10,
wherein the film exhibits a Young's modulus in the machine direction of from about 150 to about 1000 Megapascals.

20. The film of claim 19, wherein the film exhibits a Young's modulus in the cross-machine direction of from about 200 to about 1200 Megapascals.

21. The film of claim 19, wherein the film exhibits a peak elongation in the machine direction of about 200% or more and an ultimate tensile strength in the machine direction of from about 15 to about 150 Megapascals.

22. The film of claim 19, wherein the film exhibits a peak elongation in the cross-machine direction of about 700% or more and an ultimate tensile strength in the cross-machine direction of from about 15 to about 150 Megapascals.

23. The film of claim 19, wherein the nanoclay includes a montmorillonite or a salt thereof.

24. The film of claim 19, wherein the nanoclay includes platelets having an average thickness of from about 0.2 to about 100 nanometers.

25. The film of claim 19, wherein the organic surface treatment includes a quaternary onium.

26. The film of claim 19, wherein the film is multi-layered and contains a base layer and/or skin layer formed from the polymer composition.

27. The film of claim 19, wherein the first ethylene polymer includes linear low density polyethylene, low density polyethylene, or a mixture thereof.

28. The film of claim 19, wherein the second ethylene polymer includes high density polyethylene.

29. The film of claim 19, wherein the film exhibits a normalized noise level of about 2.5 or less as determined at a frequency of 4,000 Hz, wherein the normalized noise level is determined by dividing the noise level of the film by the noise level of an ambient environment.

30. A method for forming the film of claim 19, the method comprising:
melt blending the first ethylene polymer, the second ethylene polymer, and the nanoclay;
applying the polymer composition to a surface to form the film.

31. The method of claim 30, wherein the melt blending occurs in a twin screw extruder.

32. The method of claim 30, wherein the nanoclay is in the form of a powder.

* * * * *